(12) United States Patent
Hsiao et al.

(10) Patent No.: US 12,354,232 B2
(45) Date of Patent: Jul. 8, 2025

(54) SPATIOTEMPORAL RESOLUTION ENHANCEMENT OF BIOMEDICAL IMAGES

(71) Applicant: THE REGENTS OF THE UNIVERSITY OF CALIFORNIA, Oakland, CA (US)

(72) Inventors: Albert Hsiao, San Diego, CA (US); Evan Masutani, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 505 days.

(21) Appl. No.: 17/498,288

(22) Filed: Oct. 11, 2021

(65) Prior Publication Data

US 2022/0114699 A1  Apr. 14, 2022

Related U.S. Application Data

(60) Provisional application No. 63/090,154, filed on Oct. 9, 2020.

(51) Int. Cl.
| | | |
|---|---|---|
| *G06T 3/00* | (2024.01) | |
| *G06N 3/02* | (2006.01) | |
| *G06T 3/4046* | (2024.01) | |
| *G06T 3/4053* | (2024.01) | |
| *G16H 30/40* | (2018.01) | |

(52) U.S. Cl.
CPC ............ *G06T 3/4053* (2013.01); *G06N 3/02* (2013.01); *G06T 3/4046* (2013.01); *G16H 30/40* (2018.01); *G06T 2200/04* (2013.01)

(58) Field of Classification Search
CPC . G06T 3/4053; G06T 3/4046; G06T 2200/04; G06N 3/02; G06N 3/045; G06N 3/08; G16H 30/40
See application file for complete search history.

(56) References Cited

U.S. PATENT DOCUMENTS

| | | |
|---|---|---|
| 9,513,357 B2 | 12/2016 | Hsiao et al. |
| 10,398,344 B2 | 9/2019 | Beckers et al. |
| 10,600,184 B2 * | 3/2020 | Golden ............... G06T 7/149 |
| 10,628,943 B2 | 4/2020 | Hsieh et al. |
| 10,698,061 B2 | 6/2020 | Hsiao et al. |
| 10,909,681 B2 | 2/2021 | Hsiao et al. |
| 2012/0078084 A1 | 3/2012 | Piechnik et al. |

(Continued)

FOREIGN PATENT DOCUMENTS

CN    109993809 A  *  7/2019

OTHER PUBLICATIONS

Georgescu et al., Convolutional Neural Networks with Intermediate Loss for 3D Super-Resolution of CT and MRI Scans, arXiv:2001.01330v2 Mar. 12, 2020.*

(Continued)

*Primary Examiner* — Xiao Liu
(74) *Attorney, Agent, or Firm* — Eleanor Musick; Torrey Pines Law Group PC

(57) ABSTRACT

A method for improving resolution of a lower resolution image includes inputting at least one digital image into a convolutional neural network (CNN) comprising one of a SRNet and a UNet to output a two-dimensional image having a higher resolution. In some embodiments, multiple image frames may be processed using a 3D CNN to generate a two-dimensional output image.

17 Claims, 14 Drawing Sheets

(56) References Cited

U.S. PATENT DOCUMENTS

| | | | |
|---|---|---|---|
| 2014/0112564 | A1 | 4/2014 | Hsiao et al. |
| 2016/0338613 | A1 | 11/2016 | Beckers et al. |
| 2017/0045600 | A1 | 2/2017 | Asiao et al. |
| 2018/0139458 | A1* | 5/2018 | Wang ............... G06T 3/4053 |
| 2018/0256042 | A1 | 9/2018 | Beckers et al. |
| 2018/0285699 | A1 | 10/2018 | Kolouri et al. |
| 2018/0333104 | A1 | 11/2018 | Sitek |
| 2020/0311926 | A1* | 10/2020 | Tian ................. G06T 3/4053 |
| 2021/0192810 | A1* | 6/2021 | Paysan .............. G06T 7/0012 |

OTHER PUBLICATIONS

Hayat et al, Super-Resolution via Deep Learning, arXiv:1707.09077v1 Jun. 28, 2017.*

Dong et al, Image Super-Resolution Using Deep Convolutional Networks, IEEE Transactions on Pattern Analysis and Machine Intelligence, vol. 38, No. 2, pp. 295-307 (Year: 2016).*

Oktay et al, Multi-input Cardiac Image Super-Resolution Using Convolutional Neural Networks. Cham: Springer International Publishing, pp. 246-254. (Year: 2016).*

Lu et al, Super-resolution Reconstruction of Dynamic MRI by Patch Learning, ICARCV, pp. 1443-1448 (Year: 2012).*

Dezaki et al, Cardiac Phase Detection in Echocardiograms With Densely Gated Recurrent Neural Networks and Global Extrem Loss, IEEE Transactions on Medical Imaging, vol. 38, No. 8, pp. 1821-1832 (Year: 2019).*

Akkus, Z., et al., Deep Learning for Brain MRI Segmentation: State of the Art and Future Directions, J Digital Imaging; 2017; pp. 449-459.

Biglands, J.D., et al. Cardiovascular magnetic resonance physics for clinicians: part II; Journal of Cardiovascular Magnetic Resonance, 2012; 14:66; 40 pages.

Burt, J.R., et al., Myocardial T1 Mapping: Techniques and Potential Applications, RadioGraphics 2014; vol. 34 No. 2, pp. 377-395.

Girshick, R., et al., Fast R-CNN, Sep. 27, 2015, arXiv:1504.08083v2 [cs.CV] 9 pages.

Guan, Y., et al., Ensembles of Deep LSTM Learners for Activity Recognition using Wearables, Mar. 28, 2017, arXiv:1703.09370v1 [cs.LG] 28 pages.

Hasan, S.A., et al., Attention-based medical caption generation with image modality classification and clinical concept mapping, International Conference of the Cross-Language Evaluation Forum for European Languages, Springer, Cham, 2018.

Isin, A., et al., Review of MRI-based Brain Tumor Image Segmentation Using Deep Learning Methods; Procedia Computer Science, 2016, vol. 102, pp. 317-324.

Jellis, C.L., et al., Myocardial T1 mapping: modalities and clinical applications; Cardiovascular Diagnosis and Therapy 2014, vol. 4, pp. 126-137.

Karim, F., et al., LSTM Fully Convolutional Networks for Time Series Classification, IEEE Access; 2018; vol. 6., pp. 1662-1669.

Kather, J.N., et al., Color-coded visualization of magnetic resonance imaging multiparametric maps; Scientific Reports, Jan. 23, 2017, vol. 7, Art. No. 41107, 11 pages.

Kollias, D., et al., A Multi-component CNN-RNN Approach for Dimensional Emotion Recognition in-the-wild; May 3, 2018, arXiv:1805.01452v3 [cs.CV], 5 pages.

Krempl., G., et al., Workshop on Interactive Adaptive Learning (IAL), Proceedings of the European Conference on Machine Learning and Principles and Practice of Knowledge Discovery in Databases (ECML PKDD 2018); Sep. 10, 2018, Dublin, Ireland, 103 pages.

Lieman-Sifry, J., et al., FastVentricle: Cardiac Segmentation with ENet; Apr. 13, 2017; Pop M., Wright G. (eds) Functional Imaging and Modelling of the Heart, FIMH 2017, Lecture Notes in Computer Science, vol. 10263, Springer, Cham, 11 pages.

Liu, S., et al., Prostate Cancer Diagnosis Using Deep Learning with 3D Multiparametric MRI, Mar. 3, 2017, Proc. SPIE 10134, Medical Imaging 2017: Computer Aided Diagnosis, 1013428; 4 pages.

Minetto, R., et al., Hydra: an Ensemble of Convolutional NeuralNetworks for Geospatial Land Classification, Feb. 10, 2018, arXov:1802.03518 [cs.CV] 12 pages.

Padmanabhan, S., Convolutional Neural Networks for Image Classification and Captioning; spring 2016, downloaded at https://web.stanford.edu/class/cs231a/prev_projects_2016/example_paper.pdg; 8 pages.

Poudel, R.P.K., et al., Recurrent Fully Convolutional Neural Networks for Multi-Slice MRI Cardiac Segmentation, Aug. 13, 2016, arXiv:1608.03974v1 [stat.ML], 12 pages.

Prasoon, A., et al., Deep Feature Learning for Knee Cartilage Segmentation Using a Triplanar Convolutional Neural Network, MICCAI 2013, Part II, LNCS 8150, Springer-Verlag Berlin Heidelberg, Copenhagen, Denmark, 2013, pp. 246-253.

Ronneberger, O. et al., U-Net: Convolutional Networks for Biomedical Image Segmentation, May 18, 2015, pp. 1-8.

Schuhmacher, M., Autonomous anatomical structure recognition using machine learning. MS thesis. University of Twente, 2018.

Shin, H.C., et al., Interleaved text/image deep mining on a very large-scale radiology database, Proceedings of the IEEE conference on computer vision and pattern recognition, 2015.

Simonyan, K., et al., Very Deep Convolutional Networks for Large-Scale Image Recognition; Visual Geometry Group, Department of Engineering Science, University of Oxford, Sep. 2014; eprint arXiv:1409.1556.

Tran, P.V., A Fully Convolutional Neural Network for Cardiac Segmentation in Short-Axis, MRI, Apr. 27, 2017, arXiv:1604.00494v3 [cs.CV].

Wang, K., et al., Automated CT and MRI Liver Segmentation and Biometry Using a Generalized Convolutional Neural Network, Radiology: Artificial Intelligence, 2019, pp. 1-14, vol. 1.

Yasrab, R. SRNET: A Shallow Skip Connection Based Convolutional Neural Network Design for Resolving Singularities, Journal of Computer Science and Technology, Jul. 2019, pp. 924-938, vol. 34(4).

* cited by examiner

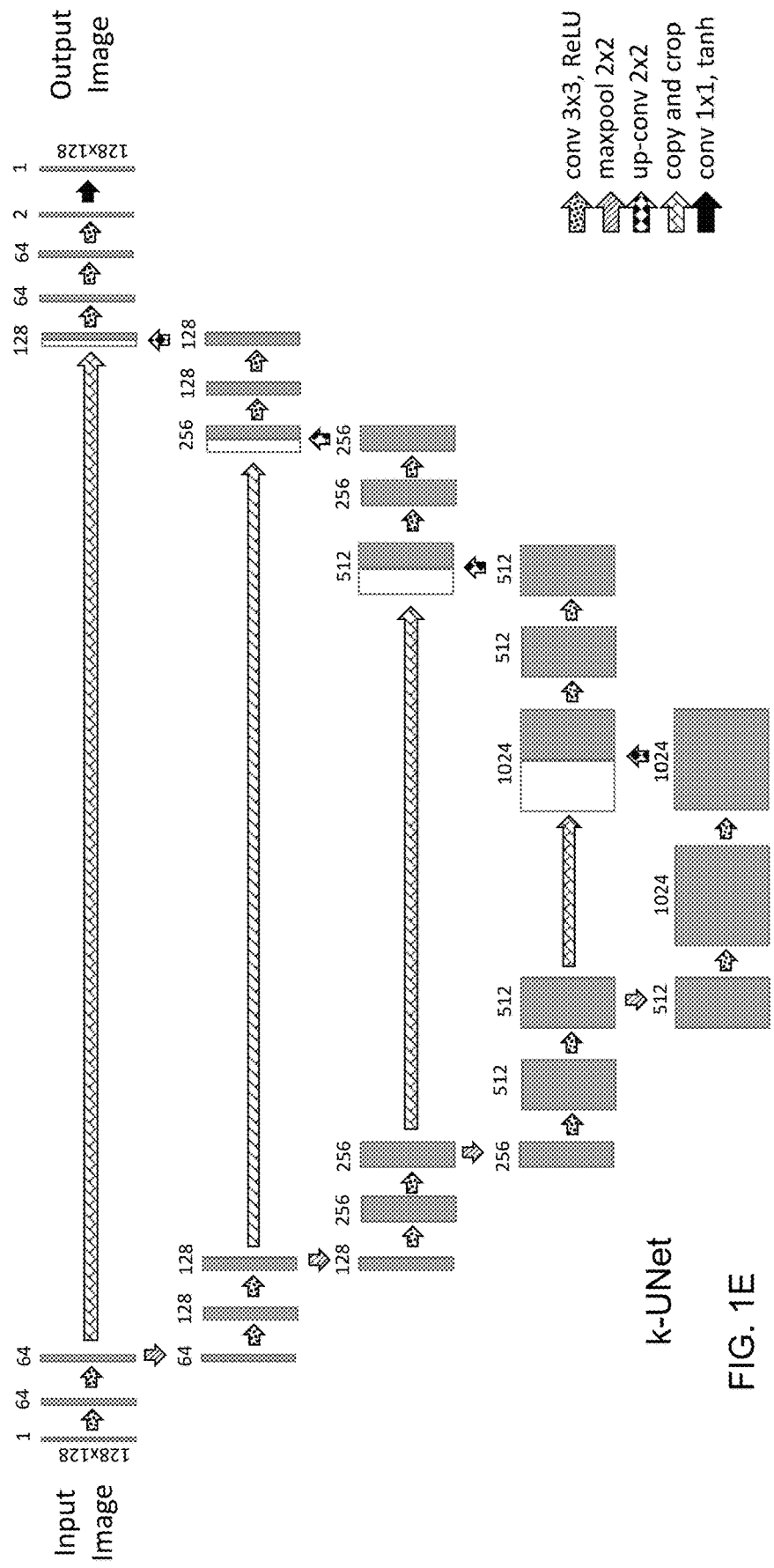
FIG. 1E  k-UNet

SPATIOTEMPORAL RESOLUTION ENHANCEMENT OF BIOMEDICAL IMAGES

RELATED APPLICATIONS

This application claims the benefit of the priority of U.S. Provisional Application No. 63/090,154, filed Oct. 9, 2020, which is incorporated herein by benefit in its entirety.

FIELD OF THE INVENTION

The present invention relates to the use of deep learning methods to enhance spatial detail from a small matrix MRI acquisition.

BACKGROUND

Cardiac MRI is essential for the evaluation of cardiac size and function and valuable in the diagnosis of cardiac disease but is limited by relatively long acquisition times. Acquisition of smaller matrix images can be performed more quickly, but at the cost of spatial detail. The advent of deep learning has reinvigorated interest in the possibility of recovering spatial detail from low resolution images, known as "super-resolution", which may enable faster acquisition of diagnostic images.

Computed tomography (CT) and magnetic resonance (MR) imaging lie at the crux of modern diagnosis and management of a wide spectrum of clinical diseases, from cardiovascular disease to cancer. In 2015, 37.8 million MRI examinations were performed. The total market size in the United States is anticipated to continue to grow to $5.6 billion by 2025. Meanwhile, total CT market size was $4.12 billion in 2017, and despite decreased reimbursements by the Centers for Medicare and Medicaid Services, total market size through 2023 is anticipated to exceed $8 billion. While the continued growth and application of CT and MRI is robust, accurate and precise diagnosis remains challenging, as the spatial and temporal resolution of modern equipment fail to achieve what is needed to fully characterize disease burden and optimally manage afflicted patients. One of the principal challenges for imaging cardiovascular and abdominal structures is the periodic motion of the heart and diaphragm, both of which lead to motion artifacts that frequently disguise culprit lesions and lead to misdiagnoses.

Cardiac MRI is the clinical reference standard for visual and quantitative assessment of heart function. Specifically, cine balanced steady-state free precession (SSFP) can yield cardiac images with high myocardium-blood pool contrast for evaluation of left ventricular function. However, MM suffers from long acquisition times, averaging over multiple heart beats requiring a tradeoff between spatial resolution, temporal resolution, and scan time. Clinically, radiologists are forced to balance acquisition time with resolution to fit clinical needs, and certain applications such as real-time imaging may require small acquisition matrices. Image scaling is typically performed using conventional upscaling methods, such as Fourier-domain zero-padding and bicubic interpolation. These methods unfortunately do not readily recover spatial detail such as the myocardial-blood pool interface or delineation of papillary muscles.

Meanwhile, advances in computational hardware and software have made it possible to apply convolutional neural networks (CNNs), a recently developed form of deep learning (DL), to a variety of biomedical problems, including imaging. CNNs are growing in popularity as a form of artificial intelligence (AI) and have been implemented to augment many facets of clinical practice, such as detecting arrhythmia, measuring heart size and function, and to automate portions of a cardiac MM. CNNs may not only be able to perform these explicit signal processing and computer vision tasks, but also further improve the technical performance of existing CT and MM equipment.

The concept of super-resolution, or recovery of high-resolution images from low-resolution observations, has been explored since the 1980s for application in video processing. A few algorithms have been proposed, which attempt to combine information between spatially-shifted and downsampled frames. However, based on physical arguments regarding the transformation between image-space and Fourier-space, multiple authors have shown skepticism that such methods are feasible. Peled, et al. ("Super-resolution in Mill: Application to human white matter fiber tract visualization by diffusion tensor imaging. *Magn Reson Med.* 2001; 45(1):29-35) and Tieng, et al. (MRI resolution enhancement: How useful are shifted images obtained by changing the demodulation frequency? *Magn Reson Med.* 2011; 65(3):664-672) attempted to combine information from multiple intersecting imaging planes, respectively, to recover spatial resolution in white matter fiber tract and phantoms, albeit with inconsistent results. It is largely believed that without prior knowledge, zero-padding (z-padding) of outer k-space is the most reliable and effective method for image upscaling, and thus is widely used as the industry standard.

CNNs have the potential to overcome some of the above-identified limitations of prior art methods. CNNs learn relevant features from input images to predict desired outputs. In medical imaging, CNNs have shown potential for image classification, segmentation, and localization for MM and CT. Importantly, CNNs have a large capacity for recalling learned features, and might supply a priori information and assumptions during inference. Based on these capabilities, CNNs should have the ability to recover high-resolution spatial detail from low-resolution images and accomplish the otherwise impossible task of single-plane super-resolution, using either a single or multiple temporal frames.

An approach based on CNNs should be able to better resolve spatial detail by leveraging the intrinsic spatiotemporal relationships that are shared across a time series. At any specific timepoint, precise anatomic detail may be clouded by motion. By analogy, a series of photographs of a child running may be motion-blurred, if the shutter speed is too slow. However, anatomic detail may subtly present in a movie comprised of multiple images. While piecing this together may be difficult to explicitly model mathematically, the proper application of CNNs can implicitly "learn" these spatiotemporal relationships and readily resolve them. For example, U.S. Pat. No. 10,909,681, incorporated herein by reference, describes the use of a CNN classifier known as "VGG19" for extracting the optimal images within a time series or other image series.

Application of this technology has the potential to touch upon many facets of diagnostic imaging, including improving the delineation of coronary anatomy for non-invasive assessment of coronary stenosis and plaque burden, speeding real-time imaging of the heart for patients with arrhythmia, or reducing the time needed to perform abdominal MM. Since the cost of many imaging technologies is related to occupancy of the equipment, reducing the amount of time required for image acquisition not only benefits the patient experience, but reduces costs, and improves availability of these limited resources for a larger number of patients.

BRIEF SUMMARY

According to embodiments of the inventive method and system, convolutional neural networks (CNNs) are used to super-resolve small acquisition matrix cardiac MR images. Among the CNNs employed, both super-resolution (SR-Nets) and UNets are quantitatively shown to outperform conventional upscaling methods at multiple upsampling factors (P<0.001). Qualitatively, CNNs appear to improve some spatial details, including the myocardium-blood pool boundary. This approach may work in vivo with prospectively acquired low resolution MR images. The invention uses a convolutional neural network to "learn" the spatial and temporal relationships that are present in a time series of medical image data from MM or CT, and then uses the neural network to increase/improve the resolution of the images. This is useful because motion usually causes artifacts in medical images, but by using this strategy, it is possible to capture low-resolution images as fast as possible, and then combine all of them together to generate a high-resolution series.

Each of the CNNs significantly outperformed traditional zero-padding and bicubic image upscaling strategies. This technology may further improve the speed of MR acquisition, particularly when challenged to acquire high-quality anatomic in patients with arrhythmia. A real-time strategy that combines multiple techniques including CNN super-resolution could lead to even greater enhancements. Earlier methods for accelerating image acquisition require certain assumptions about the sparsity of image data (i.e., compressed-sensing) or signal reception (parallel-imaging). We believe that the convolutional neural network described herein can be complementary to these technologies and further accelerate image acquisition. Furthermore, the same strategy may be applicable not only for MM but CT images as well.

The inventive neural network approach is referred to as Spatiotemporal Fourier Inverse Resolution Enhancement Network, or SptFIRE-Net. Initial experiments indicate the ability to largely reproduce native resolution images using 1/16 of the original image data, by integrating information spread across multiple time frames. Even with only 1/64 of the original image data, some image detail can be lost, but the algorithm clearly outperforms traditional image interpolation strategies (i.e., cubic interpolation) that are not able to incorporate knowledge across the time domain.

In one aspect of the invention, a method for super-resolution of a lower resolution image includes inputting at least one digital image into a computer processor configured for executing at least one convolutional neural network (CNN) for upscaling the at least one digital image to output a two-dimensional image having a higher resolution. In some embodiments, the CNN may be a SRNet neural network with a custom hybrid loss function. In other embodiments, the CNN may be a modified UNet. The digital image may be a single frame image, or it may be multiple image frames from an image time series, where the CNN is three dimensional, and the computer processor is further configured for converting a three-dimensional image generated by the CNN to output the two-dimensional image. In some embodiments, the CNN may be trained using a set of Fourier downsampled images. The at least one digital image may be a MRI or CT image. In some embodiments, the digital image is a cine balanced steady-state free precession (SSFP) series. In other embodiments, the digital image may be a short-axis (SAX) MRI.

In another aspect of the invention, a method for improving resolution of a lower resolution image includes inputting at least one digital image into a convolutional neural network (CNN) comprising one of a SRNet and a UNet to output a two-dimensional image having a higher resolution. Where the CNN is a SRNet neural network, the method further includes applying a custom hybrid loss function.

The digital image may be a single frame image, or it may be multiple image frames from an image time series, where the CNN is three dimensional, and the computer processor is further configured for converting a three-dimensional image generated by the CNN to output the two-dimensional image. In some embodiments, the CNN may be trained using a set of Fourier downsampled images. The at least one digital image may be a MRI or CT image. In some embodiments, the digital image is a cine balanced steady-state free precession (SSFP) series. In other embodiments, the digital image may be a short-axis (SAX) MRI.

The inventive methods have direct application to CT and MRI. For each modality, the inventive approach provides significant improvements in the field of medical imaging including: (a) accelerating temporally-resolved MRI to preserve anatomic detail while decreasing scan time, providing a direct benefit to patients with arrhythmia or difficulty breath-holding; and (b) augmenting temporally-resolved CT to improve anatomic detail beyond the intrinsic spatial resolution of CT, further improving diagnostic accuracy. This will directly benefit imaging and diagnosis of small structures subject to motion, such as the coronary arteries.

BRIEF DESCRIPTION OF THE DRAWINGS

FIGS. 1C-1F illustrate details for the four prototype CNNs shown in FIG. 1B trained and evaluated for single-frame and multi-frame super-resolution: k-SRNet (FIG. 1C), kt-SRNet (FIG. 1D), k-UNet (FIG. 1E), and kt-UNet (FIG. 1F), respectively, perform multi-frame super-resolution on three temporally adjacent cropped Fourier undersampled input images.

FIG. 3A plots aggregate performance for each super-resolution method. FIG. 3B plots pairwise comparison of performance between each method and zero-padding (z-pad).

In FIG. 5A, at 1.5 T, neural network methods perform well in a patient with hypertrophic cardiomyopathy. In FIG. 5B, severe RF artifact in outer k-space is repaired. In FIG. 5C, at 3T, neural network methods perform well in a patient with dilated cardiomyopathy. In FIG. 5D, the methods tolerate artifacts from sternal wires.

FIG. 6A: short-axis, low-resolution cine SSFP at 3T; FIG. 6B: 4-chamber, low-resolution cine SSFP at 3T, and FIG. 6C: an 8× undersampled photograph of a human face.

DETAILED DESCRIPTION OF EMBODIMENTS OF THE INVENTION

According to embodiments of the invention, convolutional neural networks (CNNs) are used for super-resolution to recover high-resolution images from low-resolution observations in MR and CT images. In the example implementations described herein, the inventive method provides high-frequency spatial information from short-axis cardiac MR images with superior performance compared to conventional upscaling methods. Additionally, improvement can be obtained through the use of adjacent temporal frames for multi-frame super-resolution.

Four neural networks were developed and evaluated for their ability to perform single and multi-frame super-resolution. Two general neural network architectures were explored for feasibility in performing this task. The first, a relatively shallow network is a SRCNN-inspired neural network with a custom hybrid loss function, which is referred to as "k-SRNet", based on the Shallow Wide ResNet that was described by R. Yasrab ("SRNET: A Shallow Skip Connection Based Convolutional Neural Network Design for Resolving Singularities", *Journal of Computer Science and Technology* 34, 924-938 (2019), which is incorporated herein by reference.) The second, a deeper, more complex network is a modified UNet, referred to as "k-UNet". For this network, the final activation function is set to the hyperbolic tangent; a custom hybrid loss function is employed. UNet is a fully convolutional network which is known in the art, its name derived from its u-shaped architecture, as shown. (See, O. Ronneberger, et al., "U-Net: Convolutional Networks for Biomedical Image Segmentation", (2015) arXiv: 1505.04597 [cs.CV], which incorporated herein by reference). Briefly, the UNet employs repeated application of convolutions, each followed by a rectified linear unit (ReLU) and a max pooling operation. During the contraction, the spatial information is reduced while feature information is increased. The expansive pathway combines the feature and spatial information through a sequence of up-convolutions and concatenations with high-resolution features from the contracting path. In implementations of the inventive scheme, neural networks were initially trained to perform super-resolution in image-space using synthetically-generated low-resolution data, including relatively shallow (SRNet) and relatively deep (UNet) convolutional neural networks (CNNs).

Figure 8:
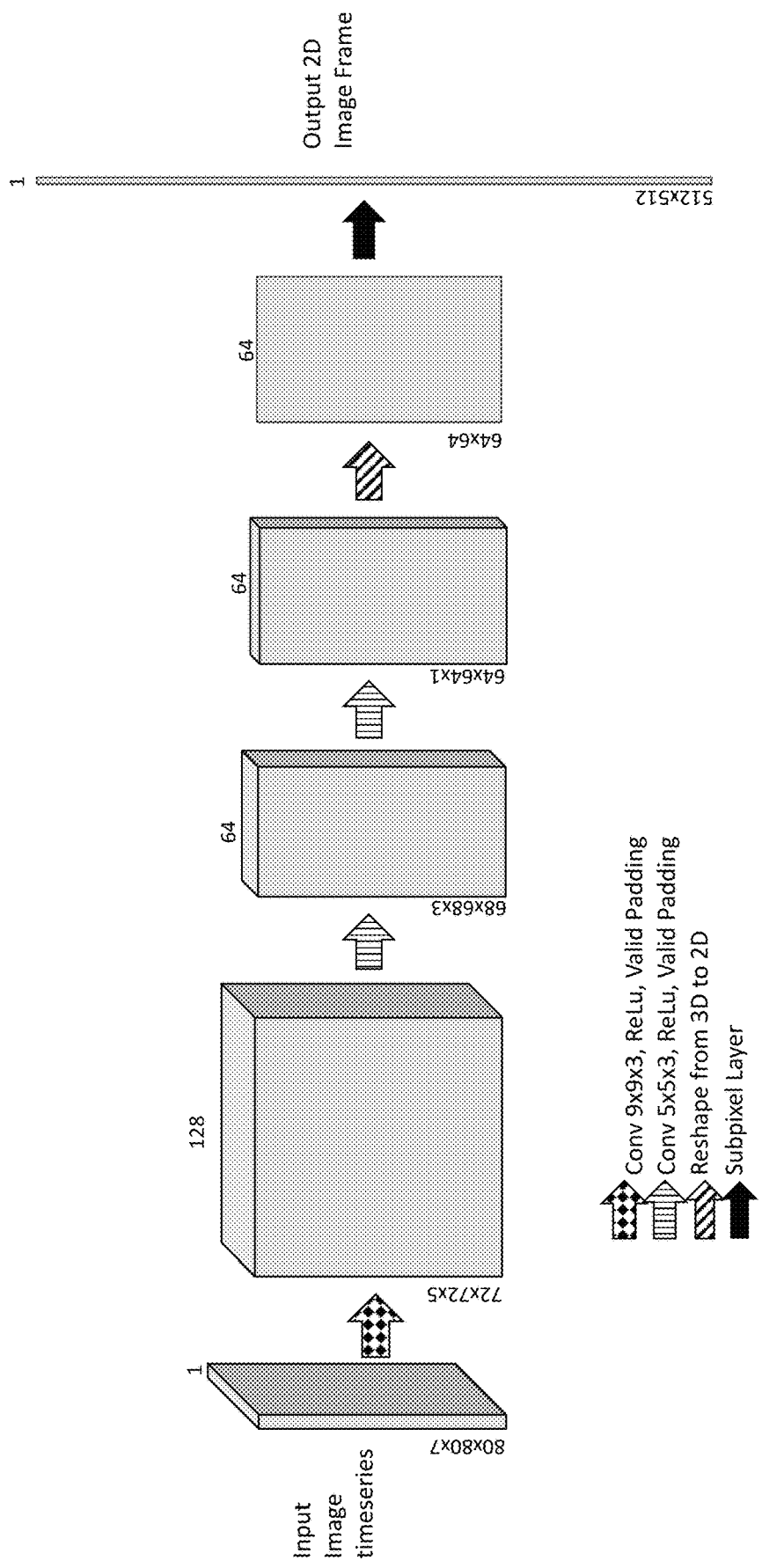
FIG. 8 is a diagram of a CNN suitable for multi-frame super-resolution according to an embodiment of the inventive method.

Further performance improvement was evaluated by training these neural networks to perform single-frame (k-) and multi-frame (kt-) super-resolution. Using the hypothesis that additional data from neighboring time points might improve performance, both architectures were extended to incorporate 3-dimensional convolutions, handling the temporal domain in the third dimension. Each input frame was combined with immediately flanking frames to generate input volumes. These spatiotemporal versions of k-SRNet and k-UNET are referred to as "kt-SRNet" and "kt-UNet", respectively. The architectures of each of these networks are illustrated in FIGS. 1B-1F where layer dimensions (e.g., 128×128) are provided beside the vertical gray bars and the numbers of channels (e.g., 1, 32, 64, etc.) are shown above the gray bars. In FIGS. 1D and 1F, the 3D gray bars in kt-SRNet and kt-UNet, respectively, emphasize use of 3D convolutions. Referring to FIG. 1C, a SRNet is shown with four convolutions: (1) conv 9×9, ReLU (rectified linear activation unit); (2) conv 5×5, ReLU; (3) conv 5×5, ReLU; and (4) conv 1×1, tanh (hyperbolic tangent activation function). This network was used for single-frame super-resolution. FIG. 1D illustrates the architecture a multi-frame SRNet with four convolutions: (1) conv 3×9×9, ReLU; (2) and (3) conv 3×5×5, ReLU, and (4) conv 3×1×1, tanh. (where the "3" represents 3D convolution, which in the evaluation involved the use of three temporally adjacent cropped undersampled input images). In the final step, the central timepoint is extracted to provide a 2D output. FIG. 8 provides an alternative architecture for multi-frame resolution with three 3D convolutions as shown to generate a 2D image.

Figure 1A:
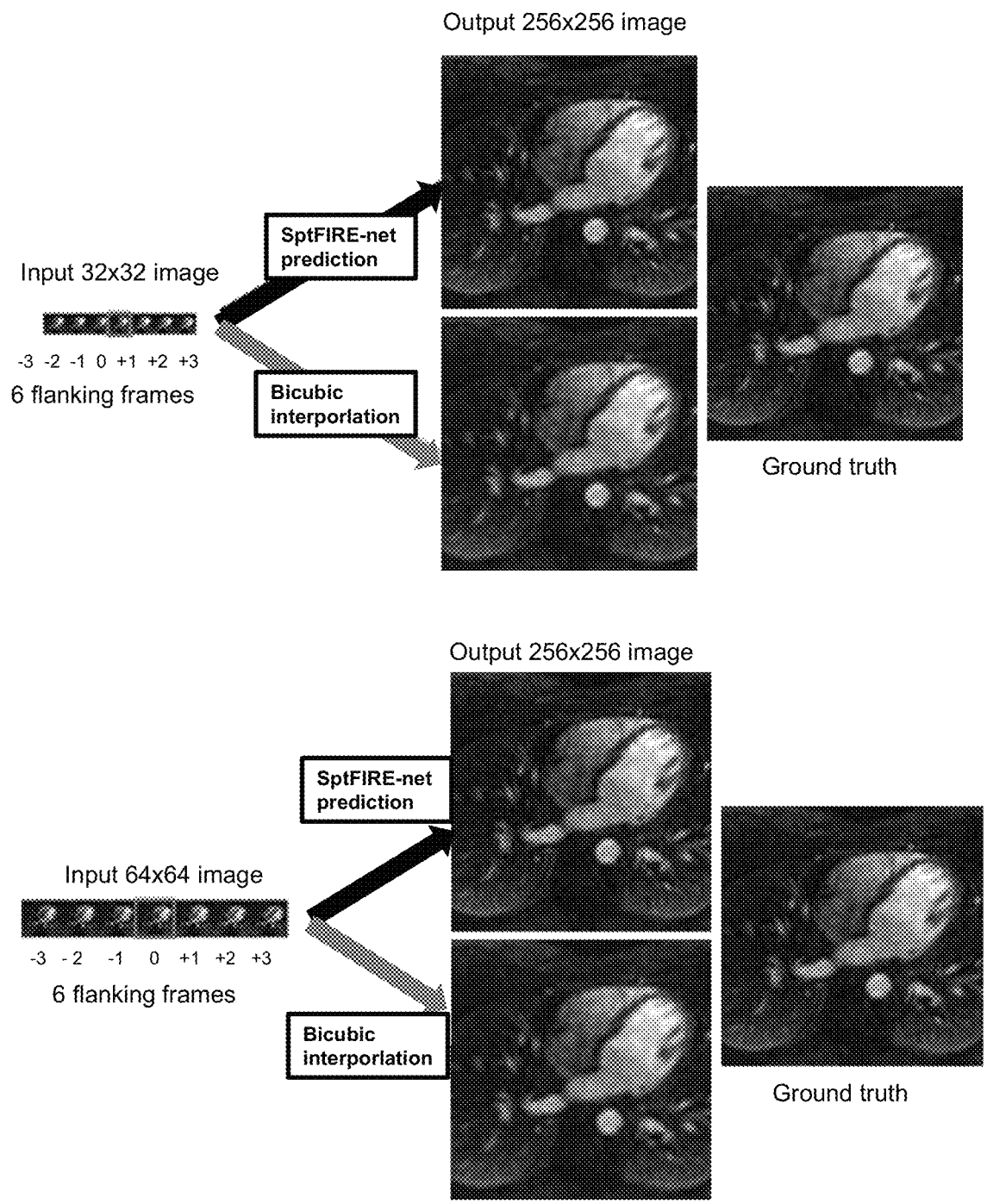
FIG. 1A illustrates the results of an initial prototype SptFIRE-Net, highlighting the ability of the CNN to extrapolate images from 64-fold and 16-fold downsampled time series.
Figure 1B:
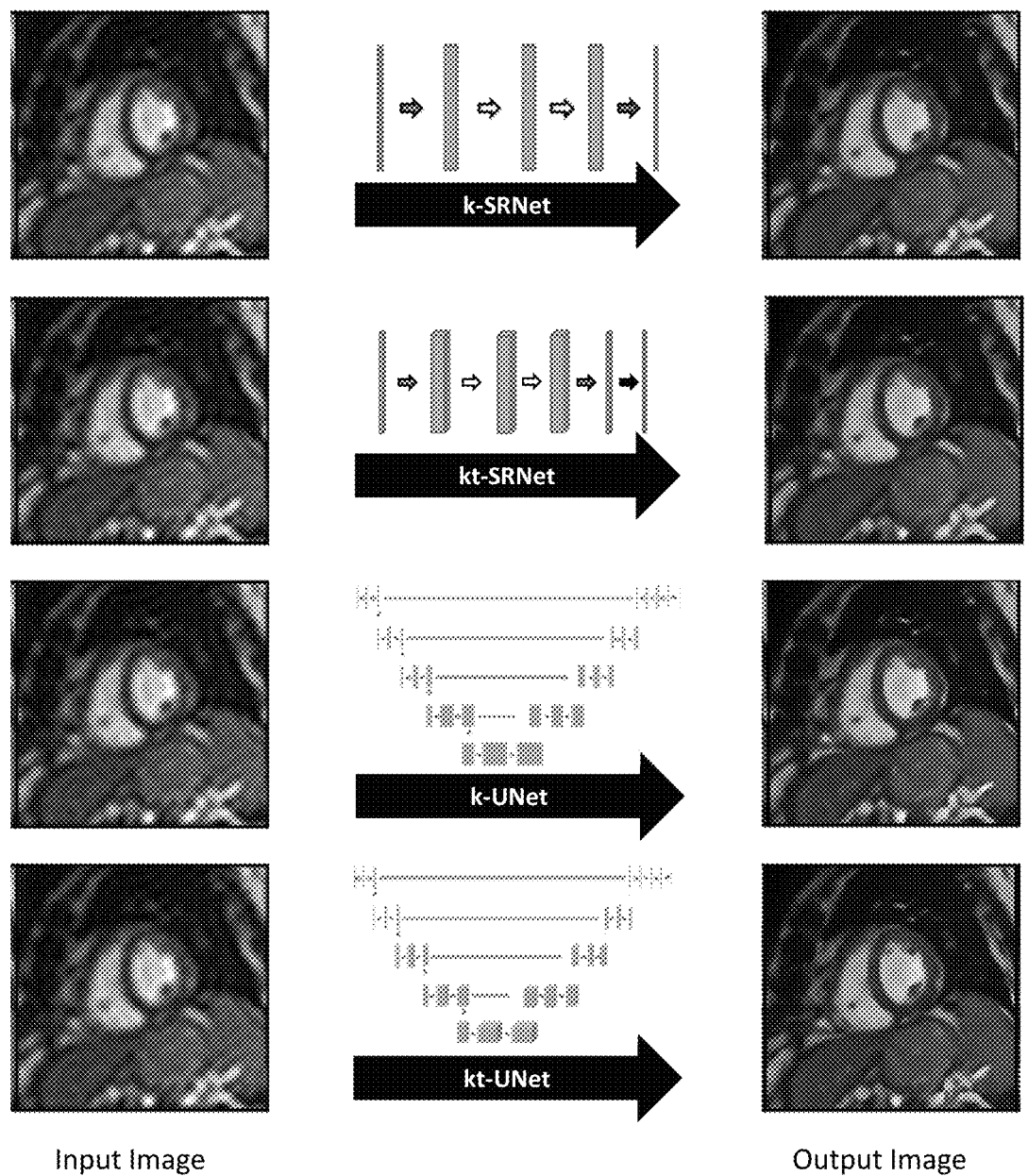
FIG. 1B illustrates prototype convolutional neural networks (CNNs) that were evaluated for their performance on single-frame (k) and multi-frame (kt) super-resolution, where k-SRNet and kt-SRNet are shallow networks and k-UNet and kt-UNet are relatively deep networks.
Figures 1C, 1D:
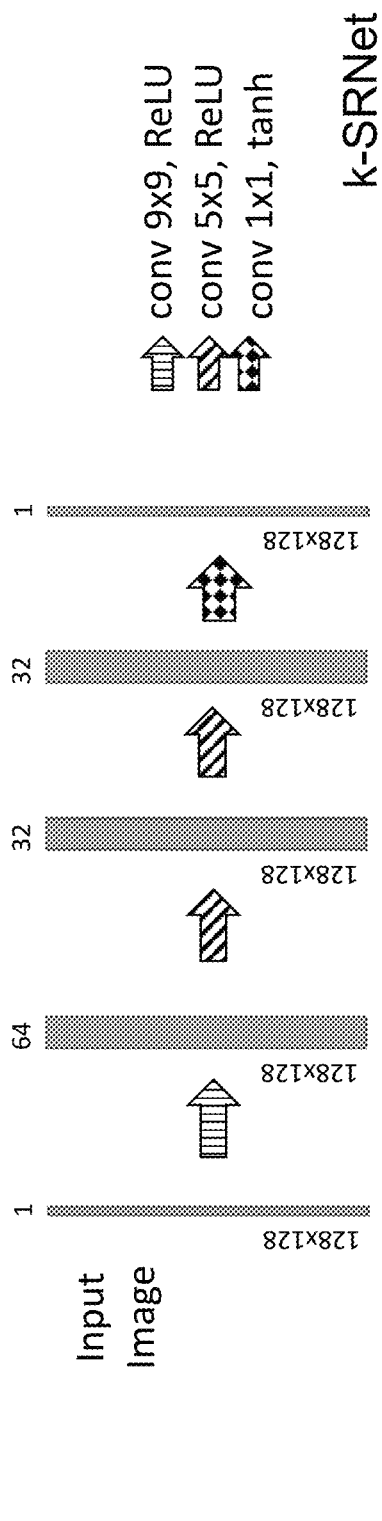
Figure 1F:
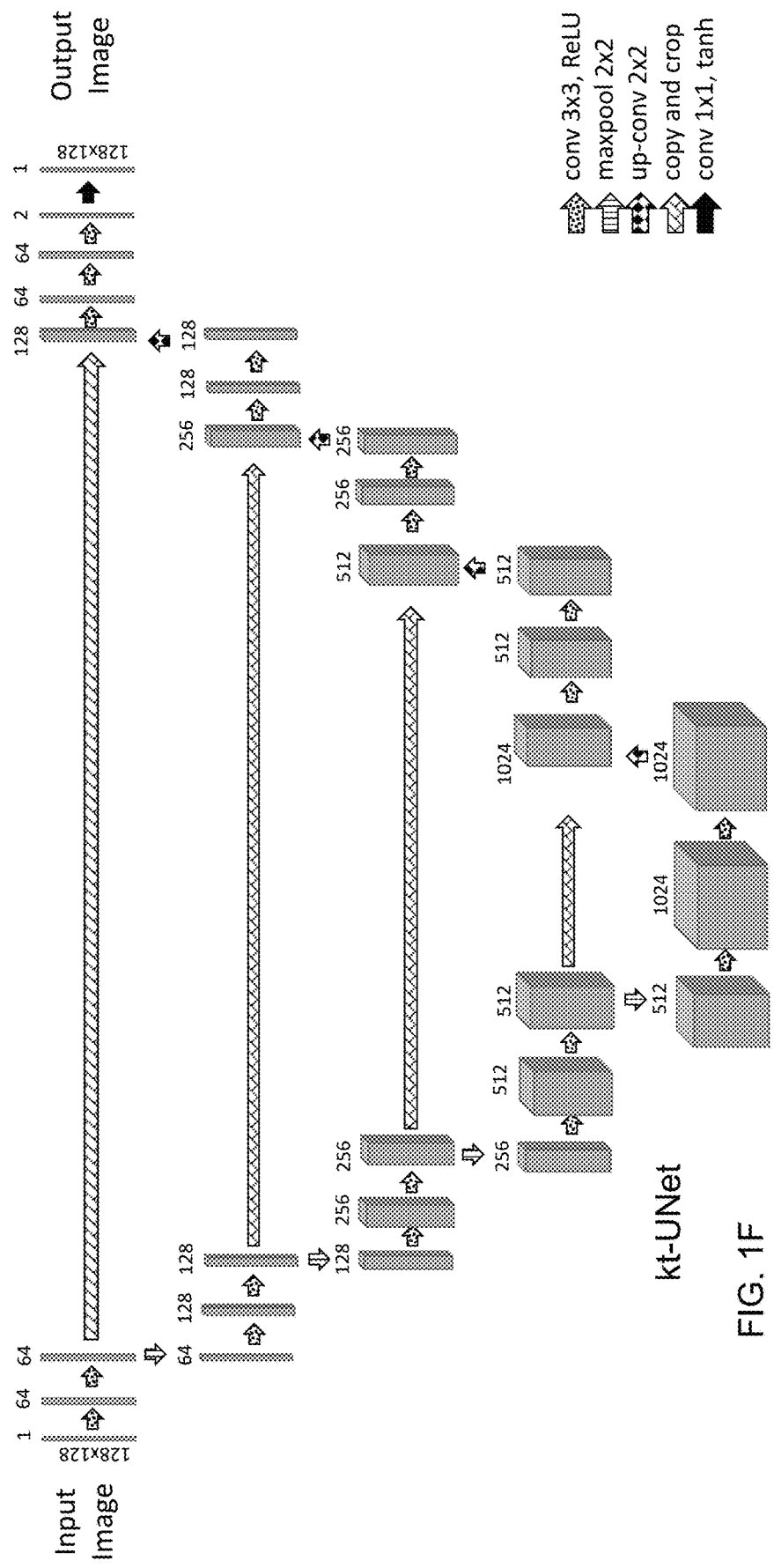

FIG. 1E illustrates the UNet used for single-frame super-resolution, where the operations (convolutions, max pooling, upconversions, and copy and crop) are specified in the figure. FIG. 1F illustrates the UNet used for multi-frame super-resolution. Again, the operations are specified in the figure.

Figure 2:
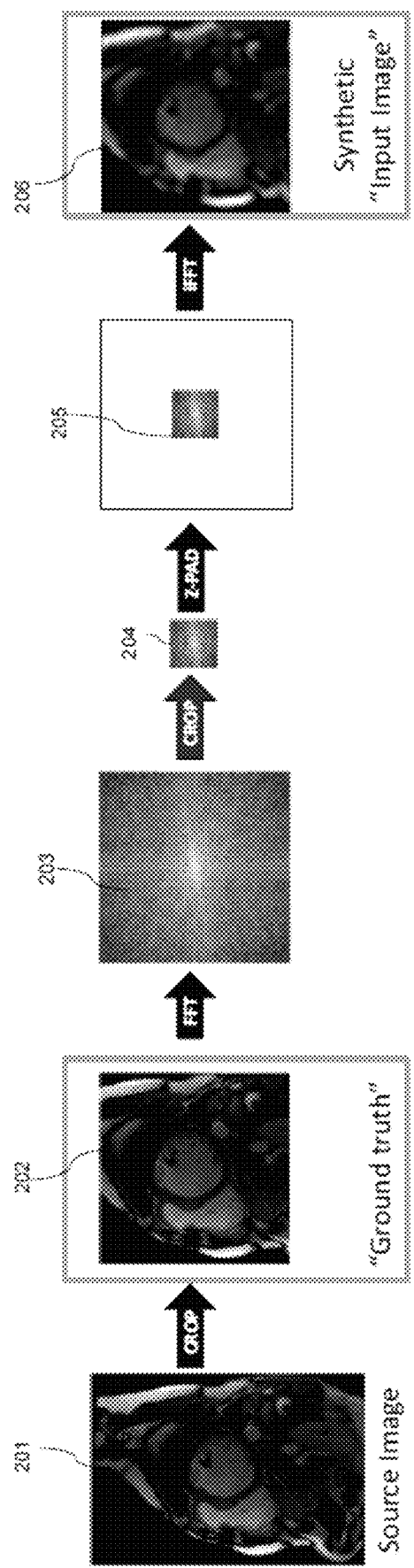
FIG. 2 diagrammatically illustrates an exemplary strategy for generation of synthetic training data.

FIG. 2 illustrates a sequence for generation and use of synthetic training data to mimic the super-resolution task. The training workflow involved cropping a central 128×128 area of the short-axis (SAX) image (source image 201) to standardize image presentation and serve as ground truth 202. To simulate low-resolution MRI acquisitions, a process referred to as "Fourier downsampling" was employed to downsample ground truth image 202 to k-space to mimic a fully-sampled, low-resolution acquisition. A FFT was applied to transform the image 202 to k-space 203. Each downsampling factor was simulated by retaining central windows of k-space of varying sizes. Outer portions of k-space 203 were cropped to k-space 204 and zero-filled to a produce a matrix size of 128×128. The resulting central region of k-space 205 which was used to generate synthetic training image 206. Images transformed back to the image domain and pixel values were scaled to [0,1]. Each downsampling (and commensurate upsampling) factor was defined as the ratio of the k-space window area to the cropped, 128×128 area.

To generate synthetic multi-frame training data, we performed the same downsampling strategy at the time frame of interest and adjacent flanking time frames. The three downsampled frames were stacked as a single volume to provide an input for the multi-frame variants of the neural networks. From this training data, the neural networks illustrated in FIGS. 1C-1F were trained to predict ground truth, effectively performing super-resolution.

Figure 9:
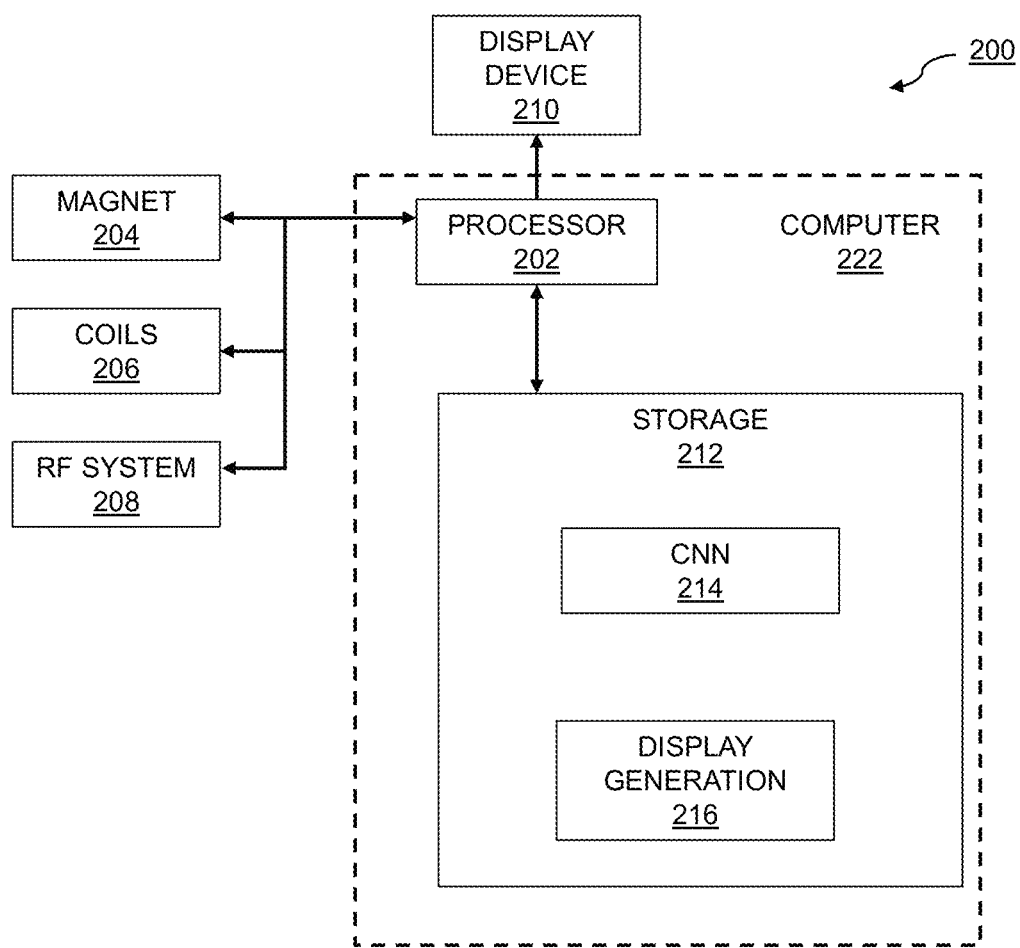
FIG. 9 is a block diagram of an exemplary imaging system in accordance with various embodiments of the invention.

FIG. 9 provides a block diagram of an exemplary magnetic resonance (MR) imaging system 200 in accordance with various embodiments. The system 200 includes a main magnet 204 to polarize the sample/subject/patient; shim coils 206 for correcting inhomogeneities in the main magnetic field; gradient coils 206 to localize the MR signal; a radio frequency (RF) system 208 which excites the sample/subject/patient and detects the resulting MR signal; and one or more computers 222 to control the aforementioned system components.

A computer 222 of the imaging system 200 comprises a processor 202 and storage 212. Suitable processors include, for example, general-purpose processors, digital signal processors, and microcontrollers. Processor architectures generally include execution units (e.g., fixed point, floating point, integer, etc.), storage (e.g., registers, memory, etc.), instruction decoding, peripherals (e.g., interrupt controllers, timers, direct memory access controllers, etc.), input/output systems (e.g., serial ports, parallel ports, etc.) and various other components and sub-systems. In the examples described herein, a GPU workstation running Ubuntu 16.04, equipped with a NVIDIA Titan V or Titan Xp GPU. The storage 212 includes a computer-readable storage medium.

Software programming executable by the processor 202 may be stored in the storage 212. More specifically, the storage 212 includes software modules comprising instructions that, when executed by the processor 202, cause the processor 202 to acquire magnetic resonance (MM) data in the region of interest ("ROI") and process it using a CNN module 214, SRNet or UNet, which module includes standard functions such as a concatenator module and a Softmax module (not separately designated), and to generate graphical images for display (module 216), e.g., on display device 210, which may be any device suitable for displaying graphic data. More particularly, the software instructions stored in the storage 212 cause the processor 202 to display the 2D super-resolution output image, possibly along with additional supporting information.

Additionally, the software instructions stored in the storage 212 may cause the processor 202 to perform various other operations described herein. In some cases, one or more of the modules may be executed using a second computer of the imaging system. (Even if the second computer is not originally or initially part of the imaging system 200, it is considered in the context of this disclosure as part of the imaging system 200.) In this disclosure, the computers of the imaging system 200 are interconnected and configured to communicate with one another and perform tasks in an integrated manner. For example, each computer is provided access the other's storage.

Patients and Image Data

Evaluation of the inventive process was conducted using a collection of 400 short axis (SAX) cine SSFP from MRI examinations performed at our institution between January 2012 to June 2017 for algorithm training and validation. All samples were obtained with HIPAA compliance and IRB waiver of informed consent. Of these 400 studies, 200 were performed on a 1.5T MRI scanner (General Electric Medical Systems Signa HDxt) and 200 were performed on a 3T MRI scanner (General Electric Discovery MR750 DV26).

For cardiac MM exams performed at 1.5T, cine SSFP series had mean flip angle of 53.58 (range: 45 to 60), mean acquisition matrix of 198×227, mean FOV of 309.40 mm (range: 136.72 mm to 440.01 mm), mean slice thickness of 8.09 mm (range: 5 mm to 10 mm), mean repetition time of 3.90 ms (range 3.44 to 4.39 ms), mean echo time of 1.69 ms (range: 1.46 ms to 1.94 ms), and a mean slice spacing of 9.52 mm (range: 5 mm to 12 mm).

For cardiac MRI exams performed at 3T, cine SSFP series had mean flip angle of 55.25 (range: 50 to 60), mean acquisition matrix of 192×190, mean FOV of 132.41 mm (range: 112.49 mm to 171.88 mm), mean slice thickness of 8.02 mm (range: 8 mm to 10 mm), mean repetition time of 3.46 ms (range 3.31 to 4.52 ms), mean echo time of 1.39 ms (range: 1.26 ms to 2.10 ms), and a mean slice spacing of 10.36 mm (range: 8 mm to 20 mm).

Neural Network Training

Short-axis images were randomly divided and allocated to 70% for training (37,700 1.5T images+32,380 3T images), 20% for validation (10,720 1.5T images+8,720 3T images), and 10% for testing (5,240 1.5T images+4,740 3T images). Networks on two workstations were trained running Ubuntu 16.04 equipped with either two Titan Xp graphics cards or one Titan V graphics card (NVIDIA; Mountain View, CA). Keras with TensorFlow-GPU backend was used for all DL experiments. For all DL networks, the Adam optimizer was used with a learning rate of 1e-4. Training with early-stopping was performed for a maximum of 25 epochs.

Hybrid Loss Function

A hybrid loss function was used based on the work of Zhao, et al. ("Loss Functions for Image Restoration With Neural Networks," *IEEE Trans Comput Imaging.* 2017; 3(1):47-57, incorporated herein by reference) Specifically, the loss function is the sum of L1-loss and a modified form of the Multiscale Structural Similarity Index (MS-SSIM) loss (defined as 1-MS-SSIM). The Tensorflow implementation of MS-SSIM and its default settings for filter size=11, filter sigma=1.5, k1=0.01, and k2=0.03 were used. Due to relatively small 128×128 matrix size for training data, only the first four default MS-SSIM power factors were used and renormalized, resulting in the weights [0.0517,0.3295, 0.3462,0.2726]. For multi-frame experiments, the 3D L1-loss was added to the mean of the MS-SSIM losses calculated for each of the three adjacent timeframes.

Model Analysis and Statistics

A unique set of UNets and SRNets were trained for multiple degrees of upsampling, from 2× to 64×. CNN-based approaches, SRNet and U-Net, and conventional methods of bicubic interpolation and z-padding were compared by calculating the Structural Similarity Index (SSIM) between each ground truth image and its corresponding super-resolved image from each method of upscaling. We report the mean and standard deviation of SSIM and determine statistical significance using paired Student's t-test with type I error threshold of 0.05.

The SSIM between the outputs of each method and the ground truth images was computed to quantitatively and objectively evaluate the performance of each super-resolution method. Python 3.5 was used for all statistical analyses. The results are listed in Table 1 and summarized in box-and-whisker plots shown in FIGS. 3A-3B. Boxes encapsulate the interquartile range, whiskers demarcate the central 95% of datapoints, and black bars lie on the median. In the figures, the boxes are color coded according to the scale shown to the right of the plots. The box colors are labeled "R" (red), corresponding to bicubic, "O" (orange) for zero-padding, "Y" (yellow) for k-SRNet, "G" (green) for kt-SRNet, "B" (blue) for k-UNet, and "P" (purple) for kt-UNet.

Figure 3A:
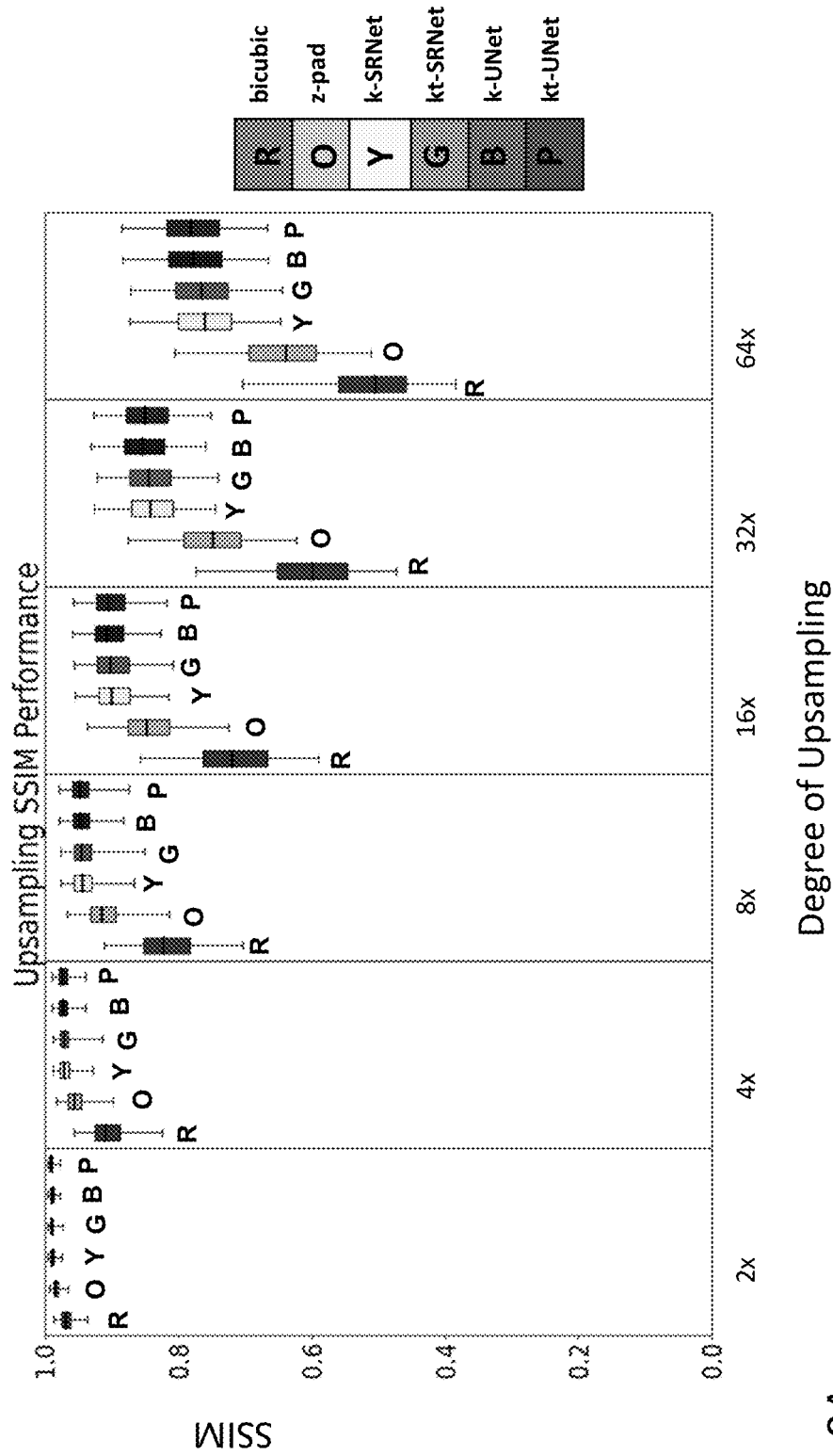
FIGS. 3A and 3B are box-and-whisker plots comparing performance (SSIM) for each super-resolution method across multiple upsampling factors.

The SSIM of shallow (SRNet) and deep (UNet) CNNs are reported as sample mean±standard deviation (n=9980) in Table 1, which provides a pairwise comparison of shallow (SRNet) and deep (UNet) methods for super-resolution. Reported SSIM values are presented as sample mean±standard deviation (n=9980). The deeper UNet appears to outperform SRNet. For all degrees of upsampling tested, every CNN outperformed conventional upscaling methods on aggregate comparison (P<0.001) (FIG. 3A).

TABLE 1

| Degree of Upsampling | k-SRNet SSIM | k-UNet SSIM | Paired t-test (k-SRNet vs. kt-UNet |
|---|---|---|---|
| SINGLE-FRAME | | | |
| 2x | 0.989 ± 0.006 | 0.989 ± 0.006 | P < 1e−7 |
| 4x | 0.969 ± 0.017 | 0.971 ± 0.016 | P < 1e−113 |
| 8x | 0.940 ± 0.027 | 0.943 ± 0.026 | P < 1e−113 |
| 16x | 0.895 ± 0.037 | 0.902 ± 0.036 | P < 1e−113 |
| 32x | 0.839 ± 0.046 | 0.850 ± 0.045 | P < 1e−113 |
| 64x | 0.760 ± 0.058 | 0.776 ± 0.058 | P < 1e−113 |
| MULTI-FRAME | | | |
| 2x | 0.988 ± 0.016 | 0.989 ± 0.023 | P < 1e−3 |
| 4x | 0.967 ± 0.036 | 0.971 ± 0.017 | P < 1e−55 |
| 8x | 0.939 ± 0.036 | 0.943 ± 0.042 | P < 1e−112 |
| 16x | 0.894 ± 0.054 | 0.898 ± 0.048 | P < 1e−86 |
| 32x | 0.840 ± 0.057 | 0.845 ± 0.054 | P < 1e−113 |
| 64x | 0.762 ± 0.068 | 0.779 ± 0.060 | P < 1e−113 |

Figure 3B:
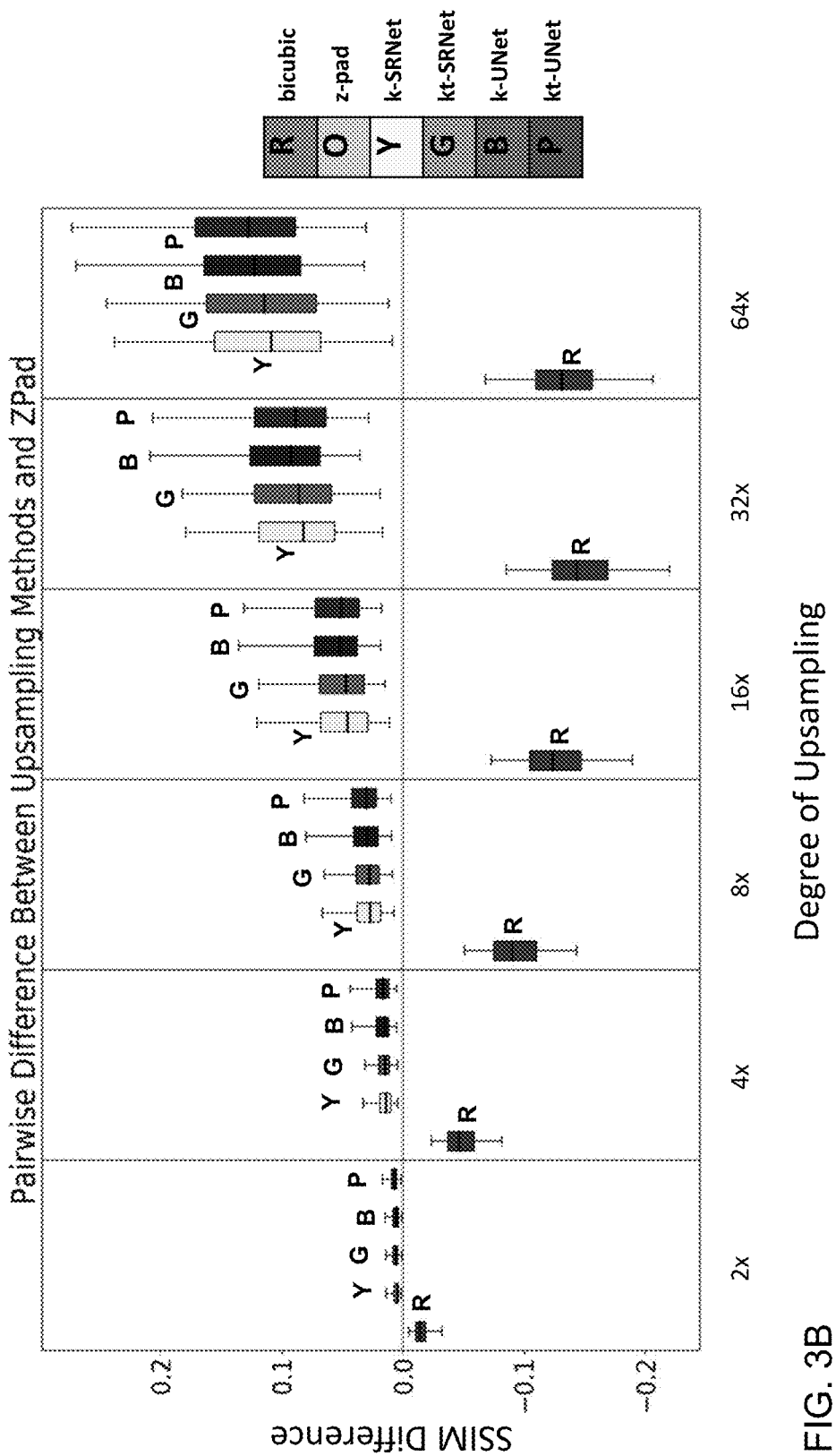

To further investigate how CNNs performed against z-padding, the per-slice difference in SSIM between z-padding and each CNN was analyzed (FIG. 3B). On a per-slice-basis, all CNNs consistently outperformed z-padding for the vast majority of input images. All four methods, k-SRNet, kt-SRNet, k-UNet, and kt-UNet, outperformed z-padding on greater than 98.5% of slices at all reported degrees of upsampling as measured by SSIM.

To explore the relative effectiveness of SRNet and the deeper UNet implementations, we then compared performance against each other using the values listed in Table 1. For synthetic test data, differences between SRNet and UNet were small, but statistically significant. For all degrees of upsampling, k-UNet and kt-UNet outperformed k-SRNet and kt-SRNet, respectively. similar performance of all CNNs was observed across upsampling factors, in contrast to a widening performance gap with conventional upscaling methods with higher upsampling factors (FIG. 3A).

The performance of each of the upsampling strategies was further explored by examining representative case examples. DL-based methods consistently outperform conventional methods on both a bulk and a per-slice basis. Neural network-based methods outperformed traditional bicubic and zero-padding for nearly every slice evaluated. Zero-padding outperforms bicubic for nearly every slice evaluated.

Figure 4:
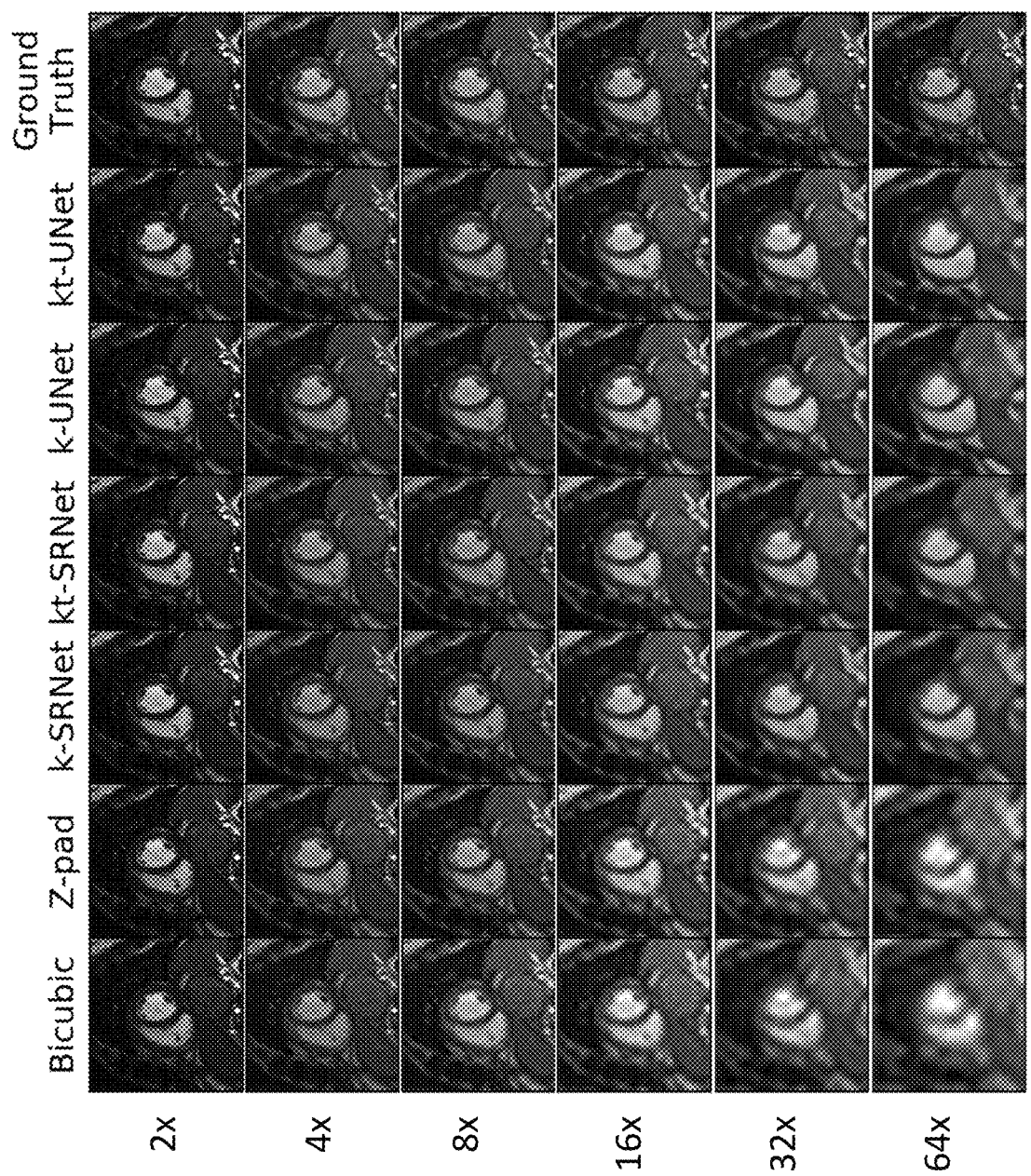
FIG. 4 provides an example comparing super-resolution methods across multiple upsampling factors from 2× to 64×.

FIG. 4 provides an example comparing super-resolution methods across different upsampling factors from 2× to 64×. At upsampling factors of 2× and 4×, the qualitative difference between each of the methods and ground truth was subtle. At 8× upsampling, bicubic interpolation showed a noticeable degradation of image quality, notably in the sharpness of the right ventricular trabeculations, and the myocardium-blood pool interface. At 16× upsampling, all methods showed noticeable image quality degradation, particularly with respect to papillary muscle sharpness; however, the edges of the interventricular septum were noticeably sharper in the CNN outputs. At 32× upsampling, the left ventricular (LV) papillary muscles appeared to blend in with the walls of the left ventricle in the bicubic and z-pad outputs. The walls of the ventricles were noticeably blurry for bicubic and z-pad. While there was some gross loss in texture of the blood pool and blurriness of the papillary muscles in the CNNs, the boundaries of the ventricular walls remained sharp. At 64× upsampling, the boundary between the right ventricular wall and the blood pool became severely blurred for the conventional upscaling methods; all papillary muscle detail was also lost. The walls and boundaries of the ventricles remained sharp in all CNNs. From upsampling factors of 8-64×, z-pad shows increasingly noticeable Gibbs artifact, which is absent in CNN predictions. The pronounced improvements obtained through the use of the inventive DL-based methods become particularly apparent at 8× and beyond.

Figures 5A, 5B, 5C, 5D:
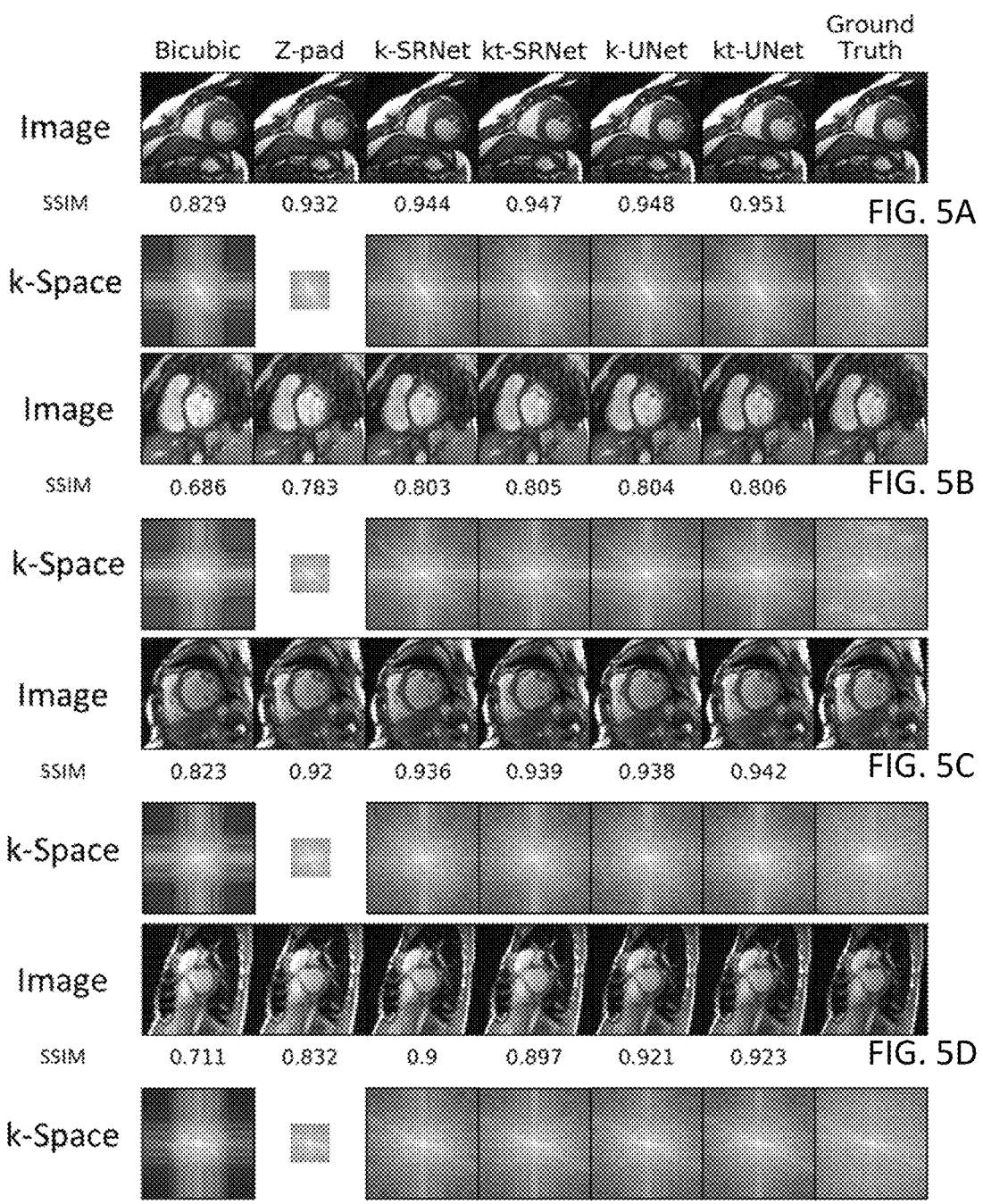
FIGS. 5A-5D are examples comparing super-resolution methods at 8× upsampling. Output images and corresponding logplots of k-space are shown along with SSIM relative to ground truth.

Representative examples, upsampled 8× with each super-resolution method, are shown in FIGS. 5A-5D. Each example shows the output image and corresponding k-space logplots for each method. In a patient with hypertrophic cardiomyopathy examined at 1.5 T (Slide 5360, 8×) (FIG. 5A), only bicubic interpolation showed reduced image quality relative to ground truth. The logplots indicated that CNNs filled outer k-space. CNNs also reduced severe RF artifacts in a 1.5T exam (Slice 7200) (FIG. 5B). Both bicubic interpolation and z-padding showed reduced sharpness at the myocardium-blood pool interface and increased graininess compared to CNN outputs. The logplots showed RF-artifact in ground truth outer k-space, which were markedly reduced in CNN predictions.

In a patient with dilated cardiomyopathy examined at 3T (Slice 320, 8×) (FIG. 5C), loss of image sharpness was observed with bicubic interpolation alone. The corresponding logplots indicated filling of outer k-space for all CNNs. CNNs also successfully super-resolved a 3T examination with artifact from sternal wires (Slice 2680) (FIG. 5D). Both bicubic interpolation and z-padding showed increased blurring of the myocardium-blood pool boundary relative to CNN outputs. SSIM of bicubic interpolation and z-padding were also markedly lower relative to CNN predictions. The logplots again indicated outer k-space filling by CNNs.

Figure 7A:
FIGS. 7A-7B show MRI examples comparing super-resolution methods at 64× upsampling. Output images and corresponding logplots of k-space are shown along with SSIM relative to ground truth. Neural network methods improve image quality at 1.5T (FIG. 7A) and 3T (FIG. 7B).
Figure 7B:
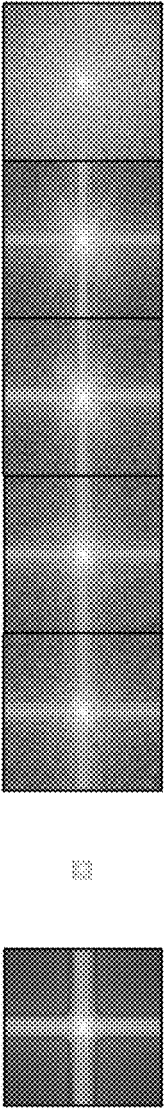

To illustrate an extreme upsampling factor, we 64× super-resolved exams at 1.5 T and 3T FIGS. 7A and 7B, respectively. All super-resolution method outputs displayed loss of detail for right ventricular trabeculations, left ventricular papillary muscles, and the blood pool; however, CNNs clearly demarcated the myocardium-blood pool boundary. CNNs also exhibited markedly higher SSIM.

Figure 6A:
FIGS. 6A-6C show proof-of-concept assessment of super-resolution methods. Undersampled acquisitions, neural network outputs, and high-resolution reference images are shown, evaluated in three conditions.
Figure 6B:
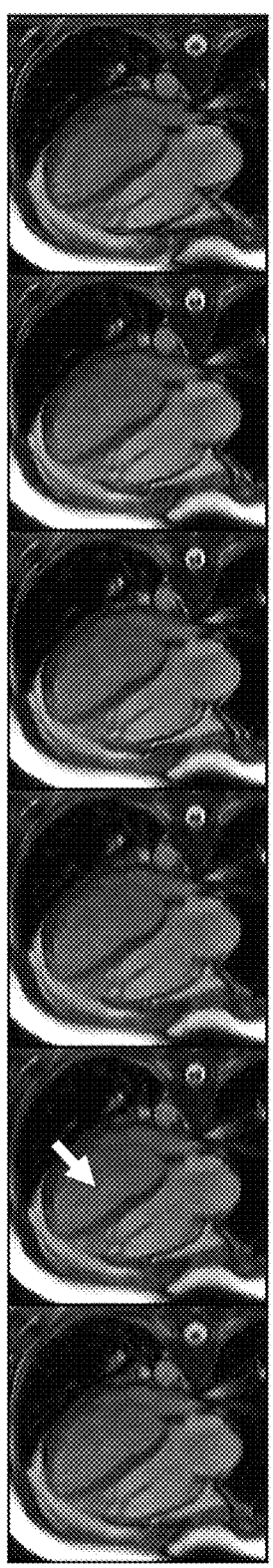
Figure 6C:
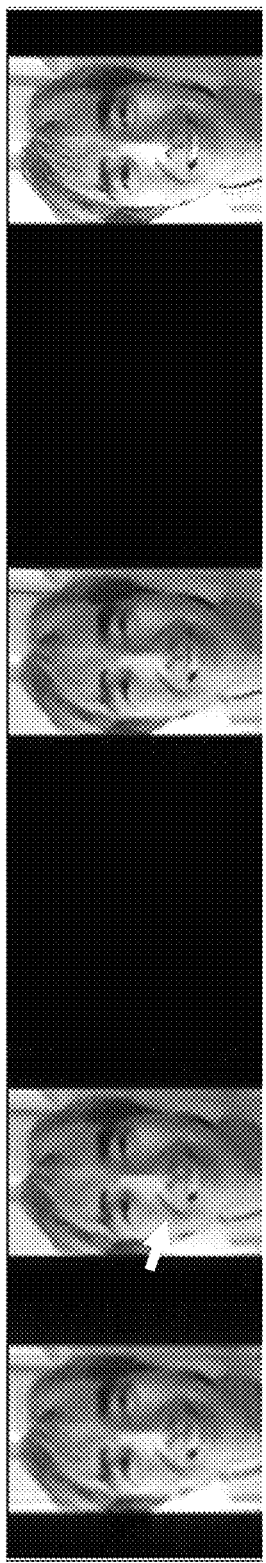

Proof-of-concept was further demonstrated by applying the CNNs on two prospectively acquired, fully-sampled low-resolution exams (FIGS. 6A-6C). Short-axis and 4-chamber cine SSFP cardiac MM exams at 3T were acquired from two healthy male volunteers aged 26 and 27 at low-resolution (92×224) and high-resolution (224×224). Images were acquired in short-axis and 4-chamber views.

To predict a high-resolution image from low-resolution inputs, outer k-space of the low-resolution acquisitions were z-padded, transformed to the image domain, retaining the central 128×128, and pixel values scaled to [0,1] prior to CNN inference.

CNNs successfully super-resolved 2.4× abbreviated 3T SAX examinations (FIG. 6A). We noted sharpening of the myocardium-blood pool interface, right ventricular trabeculations, and left ventricular papillary muscles in k-SRNet, kt-SRNet, k-UNet, and kt-UNet. The same CNNs, trained only on SAX images, also super-resolved 2.4× abbreviated 4-chamber acquisitions (FIG. 6B). k-SRNet, kt-SRNet, k-UNet, and kt-UNet increased sharpness of right ventricular trabeculations and the septal wall. While networks were trained only with short-axis SSFP images, the neural networks appear to generalize to long-axis images and digital photographs, sharpening certain details.

To further assess generalizability of the CNNs to perform super-resolution beyond cardiac MM, additional testing considered whether these neural networks could perform similar improvement on a low-resolution photographic image. Fourier downsampling was used to generate an 8× downsampled image of the human face, which is shown in the left-most frame of FIG. 6C, from the reference shown in the right-most frame of the figure. Both k-SRNet and k-UNet removed much of the ringing artifact that can be seen in the downsampled image and noticeably sharpened edges.

Based on these results, it was determined that k-SRNet, kt-SRNet, k-UNet, and kt-UNet consistently outperformed zero-padding and bicubic interpolation at all upsampling factors from 2× to 64× (p<0.001). Deeper networks, k-UNet and kt-UNet, outperformed shallower networks, k-SRNet and kt-SRNet (P<0.001). Examination of Fourier space revealed that all CNNs inferred high-frequency spatial detail from low-resolution inputs. CNNs successfully improved edge enhancement and reduced blurring on prospectively acquired low-resolution acquisitions.

CNNs outperform conventional upscaling methods and appear to recover high-frequency spatial information. Additionally, even when trained only on a small number of short-axis cardiac MR images, the inventive approach of CNN training appears to improve the quality of other imaging planes and photographic images. Summarizing the improvements provided by the inventive approach:
1) Using a strategy of training with Fourier downsampling, convolutional neural networks can consistently outperform conventional methods of image upscaling and perform single-frame or multi-frame super-resolution.
2) Though trained to perform this task purely in image-space, super-resolution CNNs appear to accomplish this task by filling outer k-space, indicating inference of high-frequency spatial detail.
3) Though trained only with synthetic data in short-axis, super-resolution CNNs appear to improve spatial detail on prospectively-acquired low-resolution acquisitions and photographic images.

The concept of super-resolution in MM has been explored in earlier studies, albeit without application of CNNs. Prior studies attempted to recover in-plane high-frequency spatial information from multiple low-resolution frames but were not successful. Many authors have felt that spatially shifted low-resolution images do not provide informational content to resolve high-frequency detail. Unlike earlier approaches, the CNNs described herein appeared to work even on a single image frame. Interestingly, the addition of multiple adjacent frames did not markedly improve performance. Without intending to be bound by theory, it appears that the CNNs described herein may achieve super-resolution based on their large feature capacity, which can carry learned information as prior knowledge. For this application, the learned information appears to generalize across multiple views, including the four-chamber view and even a photograph of a human face. Qualitatively, CNNs appear to improve some spatial details, including the myocardium-blood pool boundary. A similar approach should be applicable in vivo with prospectively acquired low resolution MR and CT images.

Clinically, super-resolution could be used to reduce scan time and/or increase temporal resolution. Acquisition time is of course, proportional to the number of phase-encode lines measured. This results in relatively long breath-holds for cardiac MRI, which cannot be tolerated by many patients. Multiple methods are now available to abbreviate acquisition, including parallel imaging and compressed sensing. Given that the inventive technique can be implemented as an image-space task, it is possible that CNN-based super-resolution may be combined with these techniques.

While the examples described herein involved the use of CNNs to super-resolve images acquired at both 1.5T and 3T at a wide range of upsampling factors, it will be apparent to those of skill in the art that they may also be used to super-resolve other views and modalities.

The invention claimed is:
1. A method for super-resolution of one or more lower resolution image, comprising:
    inputting a time series of digital images comprising spatial and temporal data into a computer processor configured for executing at least one convolutional neural network (CNN);
    training the at least one CNN using a set of Fourier downsampled images from a time frame of interest and adjacent frames flanking the time frame of interest within the time series of digital images transformed to k-space, wherein the k-space is cropped and outer k-space is zero-filled to infer high-frequency k-space data to produce a synthetic training image, wherein the synthetic training image is generated by stacking the downsampled images from the time frame of interest and the adjacent frames as a single volume to provide an input for multi-frame variants of the at least one CNN, wherein the at least one CNN is trained to predict ground truth; and
    using the trained at least one CNN, upscaling one or more digital image frame within the time series to predict a two-dimensional image having a higher resolution than the one or more digital image frame.
2. The method of claim 1, wherein the CNN is a super-resolution network (SRNet) neural network with a custom hybrid loss function.
3. The method of claim 1, wherein the at least one CNN is a modified fully convolutional neural network (UNet).
4. The method of claim 1, wherein the one or more digital image frame comprises a single frame image.
5. The method of claim 1, wherein the one or more digital image frame comprises multiple image frames from an image time series, wherein the at least one CNN is three dimensional, and the computer processor is further configured for converting a three-dimensional image generated by the at least one CNN to output the two-dimensional image.
6. The method of claim 1, wherein the one or more digital image frame comprises an MRI or CT image.
7. The method of claim 6, wherein the one or more digital image frame comprises a cine balanced steady-state free precession (SSFP) series.
8. The method of claim 6, wherein the one or more digital image frame comprises a short-axis (SAX) MRI.
9. The method of claim 1, wherein the at least one CNN is configured to infer high-frequency spatial detail and fill outer k-space using zero-padding.
10. A method for improving resolution of a lower resolution image, comprising:
    inputting a time series of digital images comprising spatial and temporal data into a convolutional neural network (CNN) comprising one of a super-resolution network (SRNet) and a fully convolutional neural network (UNet), wherein the CNN is trained using a set of Fourier downsampled images from a time frame of interest and adjacent image frames flanking the time frame of interest within the time series of digital images transformed to k-space windows, wherein the k-space windows are cropped and zero-filled to produce synthetic training images, wherein the synthetic training images are generated by stacking the downsampled images from the time frame of interest and the adjacent frames as a single volume to provide an input for multi-frame variants of the at least one CNN, wherein the at least one CNN is trained to predict ground truth; and using the trained CNN, upscaling one or more digital image frame within the time series to predict a two-dimensional image having a higher resolution than the one or more digital image frame.

11. The method of claim 10, wherein the CNN is a super-resolution network (SRNet) neural network and further comprising applying a custom hybrid loss function.

12. The method of claim 10, wherein the one or more digital image frame comprises a single frame image.

13. The method of claim 10, wherein the one or more digital image frame comprises multiple image frames from an image time series, wherein the CNN is three dimensional, and further converting a three-dimensional image generated by the CNN to output the two-dimensional image.

14. The method of claim 10, wherein the one or more digital image frame comprises an MRI or CT image.

15. The method of claim 14, wherein the one or more digital image frame comprises a cine balanced steady-state free precession (SSFP) series.

16. The method of claim 14, wherein the one or more digital image frame comprises a short-axis (SAX) MRI.

17. The method of claim 10, wherein the CNN is configured to infer high-frequency spatial detail and fill outer k-space using zero-padding.

* * * * *